(12) United States Patent
Swann

(10) Patent No.: US 8,726,905 B2
(45) Date of Patent: May 20, 2014

(54) METHODS AND DEVICES FOR OCCLUDING AN OVARIAN PATHWAY

(75) Inventor: Betsy Swann, Grass Valley, CA (US)

(73) Assignee: Bayer Essure Inc., Milpitas, CA (US)

( * ) Notice: Subject to any disclaimer, the term of this patent is extended or adjusted under 35 U.S.C. 154(b) by 19 days.

(21) Appl. No.: 13/355,148

(22) Filed: Jan. 20, 2012

(65) Prior Publication Data

US 2012/0111337 A1    May 10, 2012

Related U.S. Application Data

(63) Continuation of application No. 11/846,479, filed on Aug. 28, 2007, now Pat. No. 8,100,129.

(51) Int. Cl.
*A61F 6/06* (2006.01)

(52) U.S. Cl.
USPC .......................................... 128/831; 128/830

(58) Field of Classification Search
USPC .................. 128/830–833, 884, 887; 424/430; 606/191–193, 197–198; 600/29–31, 600/37; 623/1.12, 1.2, 1.18, 1.14, 1.15, 623/23.58, 23.72; 604/515
See application file for complete search history.

(56) References Cited

U.S. PATENT DOCUMENTS

| | | |
|---|---|---|
| 3,648,683 A | 3/1972 | Brodie |
| 3,675,639 A | 7/1972 | Cimber |
| 3,805,767 A | 4/1974 | Erb |
| 3,858,586 A | 1/1975 | Lessen |
| 4,052,754 A | 10/1977 | Homsy |
| 4,606,336 A | 8/1986 | Zeluff |
| 5,095,917 A | 3/1992 | Vancaillie |
| 5,366,756 A | 11/1994 | Chesterfield et al. |
| 5,556,396 A | 9/1996 | Cohen et al. |
| 5,601,600 A | 2/1997 | Ton |
| 5,605,693 A | 2/1997 | Seare |
| 5,935,137 A | 8/1999 | Saadat et al. |
| 5,954,715 A | 9/1999 | Harrington et al. |
| 6,096,052 A | 8/2000 | Callister et al. |
| 6,309,384 B1 | 10/2001 | Harrington et al. |
| 6,357,443 B1 | 3/2002 | Loy |
| 6,419,655 B1 | 7/2002 | Nett et al. |
| 6,432,116 B1 | 8/2002 | Callister et al. |
| 6,527,765 B2 | 3/2003 | Kelman et al. |

(Continued)

FOREIGN PATENT DOCUMENTS

| | | |
|---|---|---|
| EP | 0882428 A2 | 12/1998 |
| WO | WO 95/25490 | 9/1995 |
| WO | WO-9831308 A | 7/1998 |
| WO | WO-2005006991 A2 | 1/2005 |

OTHER PUBLICATIONS

Price, Thomas, M.D., "Permanent Transcervical Sterilization: The First 500 Women Treated in a Multi-Center Trial", http://www.adiana.com/products_overview.php, Adiana Inc., Redwood City, 1 page.

(Continued)

*Primary Examiner* — Patricia Bianco
*Assistant Examiner* — Ophelia A Hawthorne
(74) *Attorney, Agent, or Firm* — Blakely, Sokoloff, Taylor & Zafman LLP

(57) ABSTRACT

Methods and devices of sterilization by which the ovarian pathway is occluded by a plug, wherein placement of the plug may be visually confirmed. Other methods and devices are also described.

12 Claims, 14 Drawing Sheets

(56) References Cited

U.S. PATENT DOCUMENTS

| | | |
|---|---|---|
| 6,684,884 B2 | 2/2004 | Nikolchev et al. |
| 6,709,667 B1 | 3/2004 | Lowe et al. |
| 6,712,810 B2 * | 3/2004 | Harrington et al. .............. 606/28 |
| 6,726,682 B2 | 4/2004 | Harrington |
| 6,763,833 B1 | 7/2004 | Khera et al. |
| 6,780,182 B2 | 8/2004 | Bowman et al. |
| 7,014,645 B2 * | 3/2006 | Greene et al. ................. 606/158 |
| 7,329,414 B2 | 2/2008 | Fisher et al. |
| 2001/0041900 A1 | 11/2001 | Callister et al. |
| 2003/0066533 A1 | 4/2003 | Loy |
| 2004/0079377 A1 | 4/2004 | Nikolchev et al. |
| 2005/0033281 A1 | 2/2005 | Bowman et al. |
| 2005/0045183 A1 | 3/2005 | Callister et al. |
| 2005/0085844 A1 | 4/2005 | Tremulis et al. |
| 2005/0155608 A1 | 7/2005 | Pavcnik et al. |
| 2005/0192616 A1 | 9/2005 | Callister et al. |
| 2005/0209633 A1 * | 9/2005 | Callister et al. ............... 606/200 |
| 2005/0274384 A1 | 12/2005 | Tran et al. |
| 2005/0288551 A1 | 12/2005 | Callister et al. |
| 2006/0009798 A1 | 1/2006 | Callister et al. |
| 2007/0163601 A1 | 7/2007 | Pollock et al. |
| 2007/0227544 A1 | 10/2007 | Swann et al. |
| 2007/0261699 A1 | 11/2007 | Callister et al. |

OTHER PUBLICATIONS

Bowman, Brett S., "A New Transcervical Sterilization Procedure: Optimal Epithelial Ablation", http://www.adiana.com/products_overview.php, Adiana Inc., Redwood City, CA, 1 page.

Car-Brendel, Victoria E., "A New Transcervical Sterilization Procedure 6 Month Pre-clinical Results" http://www.adiana.com/products_overview.php, Adiana Inc., Redwood City, 1 page.

PCT International Invitation to Pay Additional Fees for PCT International Appln No. PCT/US2008/074682, mailed on Jan. 16, 2009 (7 pages).

PCT International Search Report and Written Opinion for PCT International Appln No. PCT/US2008/074682, mailed on Nov. 5, 2009 (22 pages).

"International Preliminary Report on Patentability", PCT/2008/074682, (Mar. 11, 2010), 13 pages.

* cited by examiner

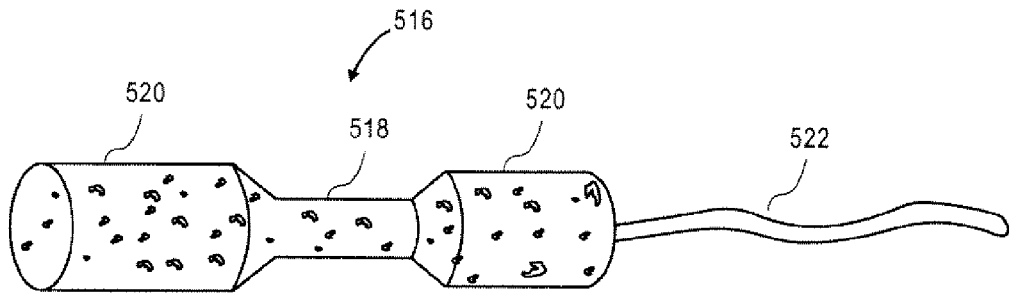
FIG. 5D
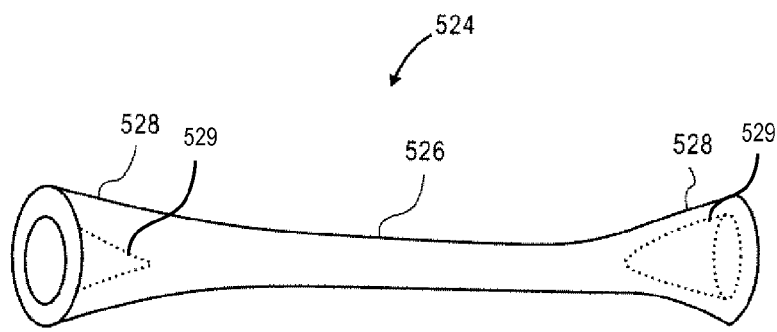
FIG. 5E
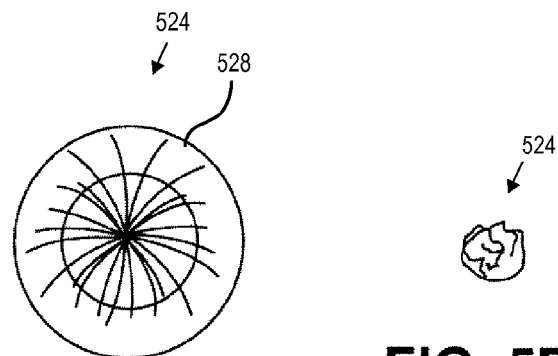
FIG. 5E I
FIG. 5E II

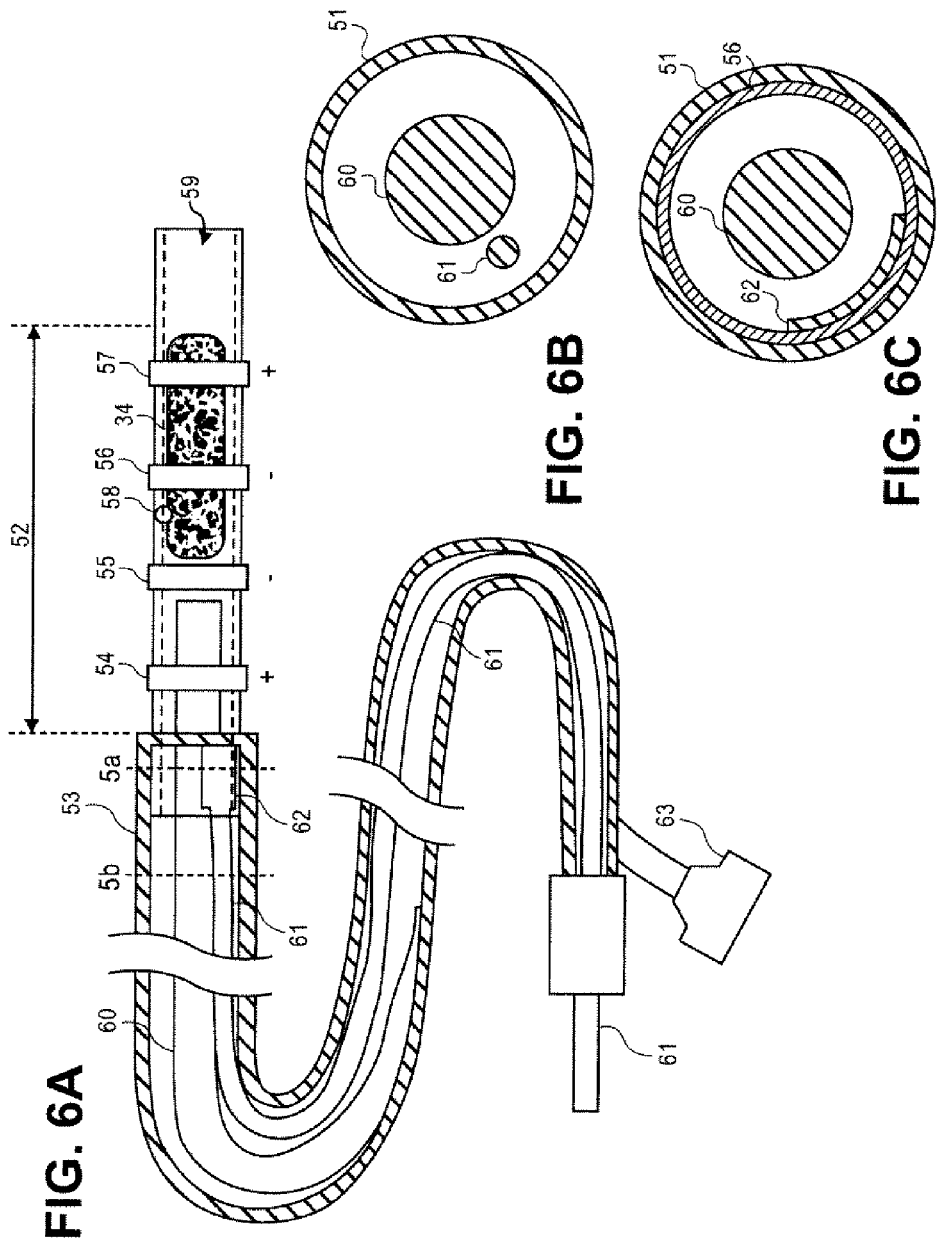

METHODS AND DEVICES FOR OCCLUDING AN OVARIAN PATHWAY

The present application is a continuation of U.S. patent application Ser. No. 11/846,479 filed on Aug. 28, 2007, now U.S. Pat. No. 8,100,129, which is incorporated herein by reference.

FIELD OF THE INVENTION

The present invention relates to an apparatus and method for permanently closing body vessels such as the utero-tubal junction, uterine isthmus, and fallopian tubes. In particular, at least certain embodiments of this invention are directed to a relatively simple surgical procedure for sterilizing human females which may be performed in the physician's office.

BACKGROUND

It is often desired or necessary for medical reasons to permanently close the fallopian tubes of women. The procedures currently proposed for occluding the fallopian tubes to effect sterilization include surgical ligation, occlusion by insertion of a foreign body, and occlusion by scarring in response to severe wounding.

One method for sterilization in females is surgical tubal ligation, a procedure in which the fallopian tubes are tied and cut, or clamped or fused with instruments passed into the pelvic cavity through an incision made through the wall of the abdomen. When done endoscopically, the pelvic cavity must be pneumatically inflated using an inert gas. Tubal ligation done with a laparotomy requires a surgical incision in the abdomen between 6 and 12 centimeters long done under general anesthesia. Currently, when the fallopian tubes are clamped or fused from the outside of the tubes, they must be clamped or fused at two or three different points in order to ensure that the tubes remain closed.

Various wounding techniques have been proposed. Cohen, et al, Method for Tubal Electroligation, U.S. Pat. No. 5,556,396 (Sep. 17, 1996) discloses a method for tubal ligation by providing an electrically energizable electrode to a fallopian tube. The electrode is advanced into the fallopian tube and energized to thermally damage the fallopian tube, thereby causing enough scarring of the fallopian tube to permanently occlude it. In another technique, a sclerosing agent (quinacrine) is injected into the uterus and fallopian tubes to create a permanent closure of the fallopian tubes.

Various plugs have been proposed for occlusion of the fallopian tubes or the utero-tubal junction. One technique involves transcervically injecting a curable elastomeric composition such as silicone into the fallopian tubes in an amount sufficient to fill the portion of the oviduct adjacent the uterus. The elastomeric composition is allowed to solidify to thereby nonsurgically block the tube. Erb, Method and Apparatus for No-Surgical, Reversible Sterilization of Females, U.S. Pat. No. 3,805,767 (Apr. 23, 1974). Others have proposed placement of an occlusive wire or coil within the fallopian tubes to occlude them. Ton, Endoluminal Coil Delivery System Having A Mechanical Release Mechanism, U.S. Pat. No. 5,601,600 (Feb. 11, 1997), proposes placement of a Guglielmi detachable coil (typically used for vascular occlusion) deep within the fallopian tube, past the isthmus. The coil must be delivered into the fallopian tubes with a delivery catheter extending from the uterus into the fallopian tubes.

Several references suggest that the fallopian tube should be damaged to the point of scarring to weld the tubes shut or to enhance retention of a plug. For example, Vancaillie, Transuterine Sterilization Apparatus and Method, U.S. Pat. No. 5,095,917 (Mar. 17, 1992) teaches a method of forming scar tissue in the fallopian tube to occlude the fallopian tube, including application of chemical scarring agents (tetracycline hydrochloride) or application of high frequency current to the fallopian tubes. The goal is to cause an immediate inflammatory reaction, including edema, arrival of white blood cells, proliferation of fibroblasts and connective tissue, and arrival of macrophages, and also to cause the subsequent healing process which leads to the formation of scar tissue in the damaged area. Lessen, Surgical Method and Electrode Therefor, U.S. Pat. No. 3,858,586 (Jan. 7, 1975) teaches the scarification of the fallopian tubes with the application of RF energy, without placement of a plug afterward, under the theory that the resulting scarring would be sufficient to seal the fallopian tubes. Both the type of injury used to initiate a lesion in the ostium/isthmus/fallopian tube and the nature of the plug material dictates the type of wound healing response that occurs. If high power is used to create the lesion, the biological response of the body will follow a typical inflammatory response and lead to creation of scar tissue.

If the plug material has an architecture, chemistry and/or pore size (smooth, non-porous materials, for example) that induces a foreign body response to the material, this will encourage the formation of scar tissue and a fibrous capsule which surrounds the plug. The foreign body response consists primarily of fibroblasts attraction to the area (including fibroblast insinuation into the plug material, if possible) and the resultant formation of connective matrix with few vascular structures. The foreign body response has also been described as "scar" formation. The cells that comprise this foreign body response can differentiate into myofibroblasts that are capable of contracting around the material and either cause the material to distort or fracture, or in the fallopian tube, dislodge the implant. The combination of the myofibroblastic contractions, peristalic movement of the tube, tubal contractions, and ciliated epithelium create a combined force capable of expulsing the material from the tube.

If the plug is inserted into a fallopian tube without the concomitant disruption of the epithelial cell lining, expulsion of the plug will usually result. The epithelial lining of the fallopian tube functions to protect the underlying layers from infiltration and infection by foreign substances and infectious agents. In the same way, few cells will traverse the epithelial lining to enter the lumen of the fallopian tube, where the plug resides. Thus, implanting a plug in an intact tube results in little, if any, infiltration unto the plug material. Instead, it is likely that a non-infiltrated large pore plug would become a receptacle for necrotic debris shed within the fallopian tube. This could result in higher contamination and infection of the plug matrix. Additionally, the lack of ingrowth would result in less anchoring of the plug matrix, so the expulsion forces present within the fallopian tube could dislodge and expulse the plug. Thus, retention of an intact epithelial layer is not desired, and the epithelial cell layer must be destroyed or disrupted to eliminate the physical barrier to infiltrating cells. After this has occurred, a porous material can be placed into the denuded area, and a wound healing response can follow. Implanting porous materials into a fallopian tube that has an intact epithelial lining does not allow ingrowth into the material, as part of the epithelial cell lining's function is to act as a physical barrier to infectious agents and cellular infiltrate.

Prior patent application, Harrington et al, Method And Apparatus For Tubal Occlusion, U.S. application Ser. No. 09/063,119, (filed May 20, 1998) (the disclosure of which is incorporated herein by reference) illustrates a method blocking off the fallopian tubes by placing a plug in the ostium or cornu of the uterus leading into the fallopian tubes. An exemplary embodiment discussed in this application was the application of heat to damage the tissue of the ostium and place a plug into the ostium which, was secured into the ostium by the inflammation of the ostium caused by the thermal injury. The proposed plug comprised a foamed material which permitted the ingrowth of tissue into the plug.

U.S. Pat. Nos. 6,309,384 and 6,780,182 illustrate a method and apparatus for placing a foam plug in the fallopian tubes, the disclosure of which is incorporated herein by reference. Implanted devices similar to what is disclosed in the above patents, manufactured by Adiana, Inc., Redwood City, Calif., USA, have been used in attempts to sterlize patients. A recent study, from the EASE clinical trial, has shown that the devices were not always bilaterally (both fallopian tubes) successful in preventing pregnancy. Problems with devices as illustrated above include poor visualization, as the devices lack a visual identifier to confirm a successful insertion from an endoscopic view. Thus when no part of the device is visible, a physician must go on faith that an implant is successfully inserted into a fallopian tube. With no visual indicator a physician may also mistakenly implant two devices in one fallopian tube, which is described as a unilateral placement. Prior devices also lack any indicators for viewing under x-ray, thus it is very difficult to visualize proper placement on patient follow-up visits using x-ray examination.

SUMMARY OF THE DESCRIPTION

The invention includes methods and devices for occluding ovarian pathways. According to one aspect of the invention, an embodiment of a method may include delivering a catheter device into an ovarian pathway, the ovarian pathway having a ostium, wounding the ovarian pathway with the catheter device at a point beyond the ostium, delivering a plug including a visual marker into the wounded segment of the fallopian tube, wherein the plug is delivered from the catheter device, and visually confirming the placement of the plug by observing the presence of the visual marker about the ostium. This visual confirmation may occur after the catheter is withdrawn from the ostium According to an another aspect of the invention, an embodiment of a device may include foam plugs for occlusion of an ovarian pathway, including a foam body, wherein the foam is designed to promote ovarian pathway tissue ingrowth into the foam body; and an elongated tail marker coupled to the foam body. The foam body may further include an imaging contrast substance or substances such as echogenic (for ultrasound imaging) substances or radiopaque (for x-ray imaging) substances or a combination of both echogenic and radiopaque substances. These substances may be implanted or integrated into the foam body and allow for confirmation of the position of the foam body by the appropriate imaging method.

According to an another aspect of the invention, an embodiment of a device may also include an elongated catheter with a lumen disposed therein, with an inner pusher slidably housed within the lumen, and at least two occlusion devices, each designed to occlude an ovarian pathway, slidably housed within the lumen and adjacent to the inner pusher, and a marker element slidably housed between the occlusion devices.

According to an another aspect of the invention, an embodiment of a method may also include delivering a catheter device into a first ovarian pathway with an endoscope device, delivering a first occlusion device into the first ovarian pathway, confirming delivery of the first occlusion device by ejecting a marker element from the catheter device, delivering the catheter device into a second ovarian pathway with the endoscope device, and delivering a second occlusion device into the second ovarian pathway.

According to an another aspect of the invention, an embodiment of a method may also include delivering a catheter device into an ovarian pathway with an endoscopic device, the fallopian tube having an ostium, delivering an elongated foam occlusion device into the ovarian pathway, wherein after delivery a visible portion of the elongated foam occlusion device is the proximal to the ostium; and confirming delivery of the elongated foam occlusion device by observing the visible portion of the elongated foam occlusion device.

According to an another aspect of the invention, an embodiment of the device may include an elongated foam plug, wherein the foam plug is designed for placement in an ovarian pathway and includes a tear-away joint.

According to an another aspect of the invention, an embodiment of a method may also include observing a tail portion of a plug exiting out of a ovarian pathway; and removing the tail portion of the plug.

BRIEF DESCRIPTION OF THE DRAWINGS

The present invention is illustrated by way of example and not limitation in the figures of the accompanying drawings in which like references indicate similar elements.

FIG. 5d is a side view of an elongated plug.

FIGS. 5e, 5eI, and 5eII are side, end, and compressed end views of an elongated plug, respectively.

FIG. 6a is a drawing of the device used to deliver RF power and an occluding plug to the utero-tubal junction.

FIGS. 6b and 6c show the cross sections of the device illustrated in FIG. 6a.

FIG. 6d shows a cross section of an alternate construction of the device illustrated in FIG. 6a.

FIGS. 6e and 6f show cross sections of an alternate construction of the device illustrated in FIG. 6a.

DETAILED DESCRIPTION

Various embodiments and aspects of the inventions will be described with reference to details discussed below, and the accompanying drawings will illustrate the various embodiments. The following description and drawings are illustrative of the invention and are not to be construed as limiting the invention. Numerous specific details are described to provide a through understanding of various embodiments of the present invention. However, in certain instances, well-known or conventional details are not described in order to provide a concise discussion of embodiments of the present inventions.

Figure 1:
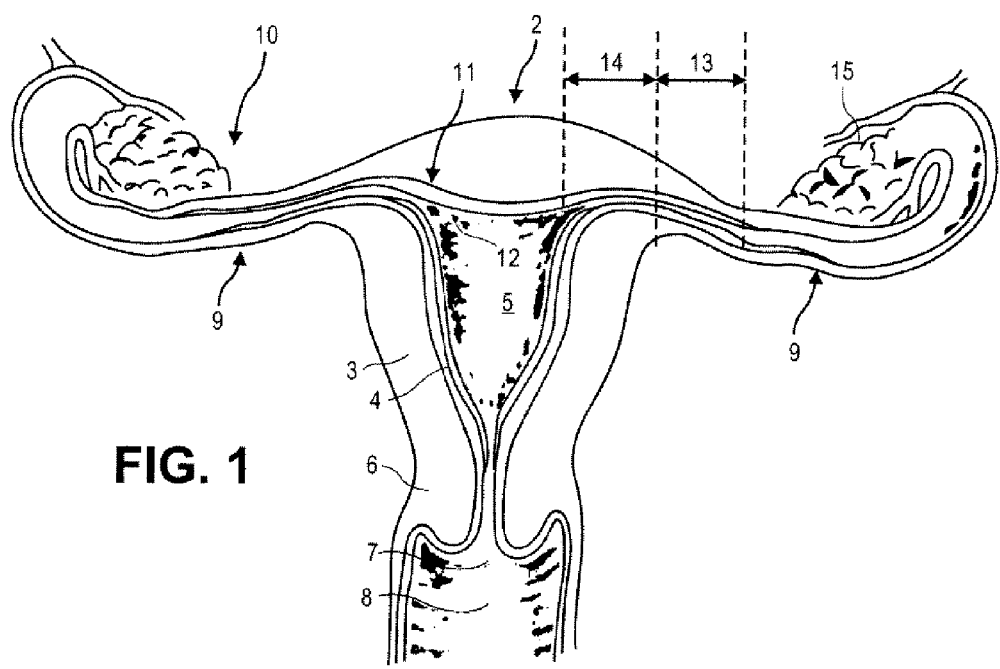
FIG. 1 is a partial view of the female reproductive system.

FIG. 1 shows some of the major elements of the female reproductive system. The uterus 2 is an organ of the female pelvis that has the shape of a pear. It consists of a thick muscular coat, the myometrium 3, a cavity having an inner mucosal lining of variable thickness called the endometrium 4, and a cavity referred to as the uterine cavity 5. The cervix 6 defines the cervical canal 7 which is an inferior opening to the vagina 8. The fallopian tube (or ampulla) 9 is a hollow organ that connects the uterus to the ovary 10. The ovary 15 is the organ that produces one or more eggs during every cycle of a woman's reproductive life. In the human female reproductive system, there is one uterus, two fallopian tubes and two ovaries (under normal conditions). The site where the fallopian tube and uterus connect is called the utero-tubal junction 11. It is a section of tubular shape of about 10 mm in length. Its inner diameter in the resting position is less than 1 mm, but when gas or liquid is pushed through the uterus and tubes, the diameter of the utero-tubal junction may stretch up to about 2 mm. The utero-tubal junction provides a transition between the uterus and the fallopian tube, and the area of transition from the chamber of the uterus to the lumen of the utero-tubal junction is referred to as the ostium or cornu (marked with item number 12). The area of transition between the ostium and the isthmus 13 of the fallopian tube is referred to as the interstitial portion (marked as item 14). The ostium, utero-tubal junction, interstitial portion, isthmus and fallopian tube are part of a pathway leading from the ovaries to the uterus, and this pathway is sometimes referred to as the uterine tube. For the sake of clarity the term ovarian pathway is to denote the entire passageway through which the ova pass when transiting from the ovaries to the uterine cavity.

Figure 2:
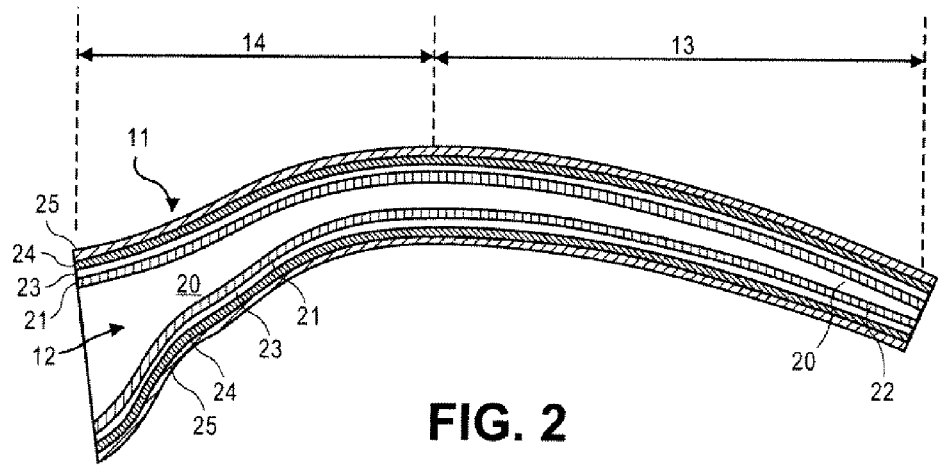
FIG. 2 is a cross section of the utero-tubal junction of the female reproductive system.

FIG. 2 shows the utero-tubal junction 11, including the ostium 12, the isthmus 13, and the interstitial portion 14. The cross section shows the layers of tissue that make up the utero-tubal junction. The lumen 20 passes through the fallopian tube, and this lumen is lined with a layer of mucosal tissue consisting of epithelium 21 and lamina propria 23. Within the fallopian tube, this layer of mucosal tissue is referred to as the endosalpinx, indicated as item 22. The layer of tissue under the epithelial layer is the lamina propria, indicated as item 23. The lamina propria is surrounded by a layer of circular muscle 24 which is surrounded by layer of longitudinal muscle 25. The longitudinal muscle layer may be surrounded with a second layer of circular muscle. The first circular muscle layer 24 typically comprises about 10-14 layers of muscles cells. One aspect of the new treatment method is the extent to which each of these layers is damaged prior to insertion of an occluding plug.

Figure 3A:
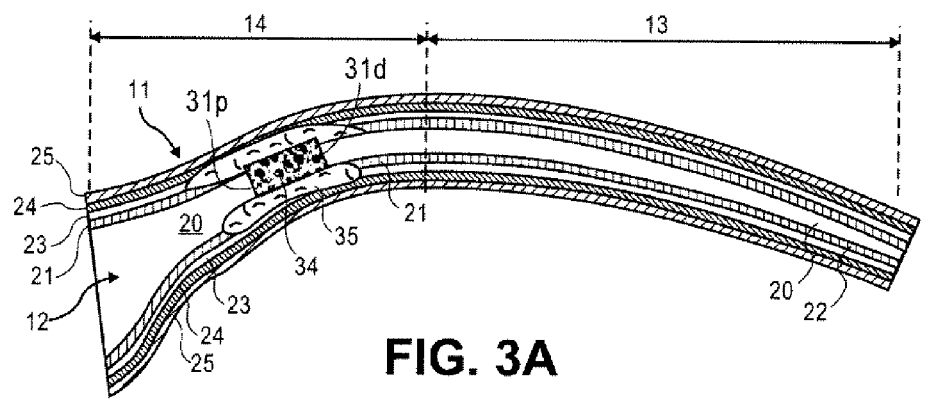
FIGS. 3a and 3b are cross sections of the utero-tubal junction of the female reproductive system with an organiod plug in place.

FIG. 3a illustrates the desired degree of damage in each layer of the utero-tubal junction, and the desired interaction between the tissue and the foam plug which is inserted to generate an occlusion of the fallopian tube. The foam plug 34 is inserted into the target site for occlusion, which in this illustration is the utero-tubal junction. The plug is put in place after the target site has been treated with the application of thermal energy. The thermal energy is delivered at levels well below the level required to cause a severe burn (and the concomitant severe inflammatory response), but sufficient to cause thermal necrosis of the epithelial layer 21 and the lamina propria 23. The area of thermal death (necrosis) is indicated as item 35, and extends for a length of approximately 4 to 10 millimeters along the pathway. Damage to the circular muscle layer 24 is acceptable, but damage to the longitudinal muscle layer 25 is undesirable. This leads to minimal collapse of the utero-tubal junction about the plug. The body responds with normal "wound healing response." The term "wound healing response" is a term understood in the art to include biological activities including: (1) arrival of leukocytes, neutrophils, monocytes, and their transformation into macrophages and aggregation into giant cells, and arrival of fibroblast cells, (collectively referred to as inflammatory cells), and (2) the creation of an extracellular matrix and deposition of proteins, and (3) the formation of granulation and connective tissue at the wound site.

The wound healing response may continue to completion in the surrounding intact pathway, and will further entail reorganization of the granulation tissue into specialized and functional tissue corresponding to the original injured tissue (matching the architecture of the original tissue), and the formation of scar tissue (different from the tissue's original architecture). The tissue response immediately surrounding the plug depends on the composition, pore size and architecture of the plug. For the plugs described below, the short term and long-term condition of the tissue immediately surrounding the plug and/or in-growing within the plug depends on the pore size and architecture of the plug. Where the pore size is large relative to the cell size, in the range of 40-200 micron, and of a specific architecture, the body will heal by forming a vascularized tissue within the pores of the foam. Inflammatory cells will enter the foam pores, attract other cells, form extracellular matrix and connective tissue, and form into a collection of tissue referred to as granulation tissue within the pores of the foam. Subsequent healing includes in-growth of vascular structures such as arterioles, capillaries and lymphatic vessels into the connective tissue residing within the pores of the foam. Because of the unique architecture and pore size of the foam, the granulation tissue will remain as granulation tissue indefinitely. Thus the large pore plug, in its final form within the body, will comprise numerous filaments of the foam superstructure which form a network of communicating pores, with granulation tissue occupying the pores. The plug will also comprise numerous blood vessels formed within the granulation tissue, so that the tissue interspersed with the original plug material may be described as vascularized organic tissue. The vascularized tissue is vascularized to the same extent as is typical of other natural organs within the body.

Where the plug pore size is small compared to cell size, in the range of 1-20 microns, vascularized granulation tissue will not form in the plug interstices. Subsequent healing includes formation of a highly vascularized foreign body capsule and intrusion of some macrophages into the plug pores, without intrusion of other cells or tissue associated with the later stages of healing (such as extracellular matrix, granulation tissue and blood vessels). Instead, the body will form a vascularized capsule with blood vessels closely approaching the plug, lying adjacent and within about 10 um of the foam. This may be referred to as an altered foreign body response.

Figure 3B:
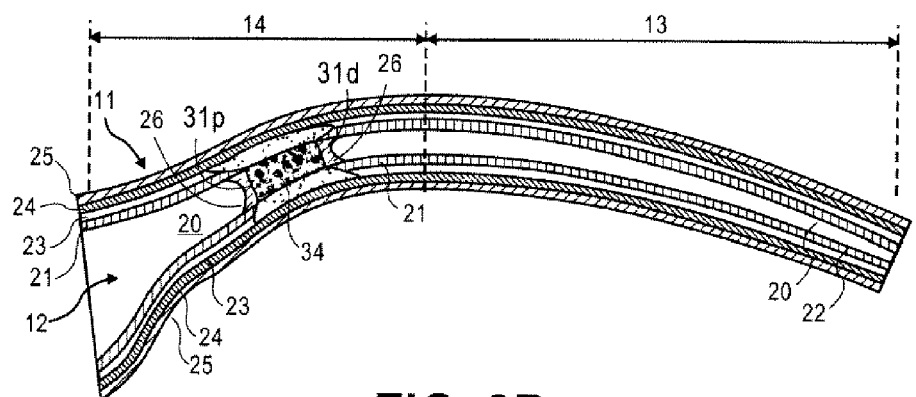
Figure 3C:
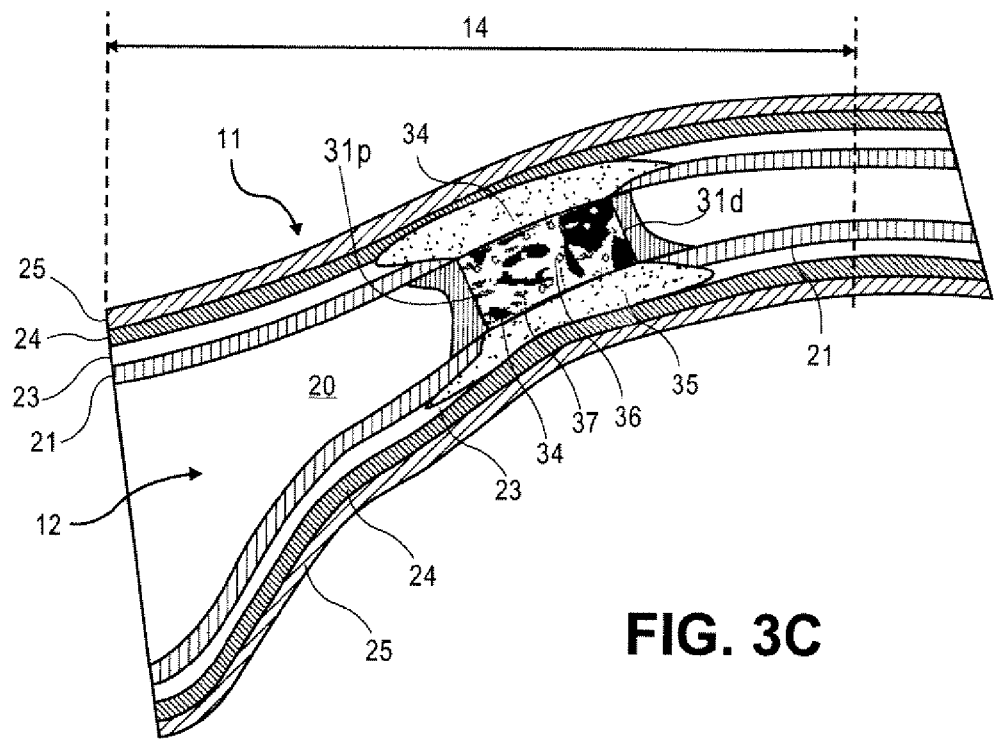
FIGS. 3c and 3d illustrate the boundary response of wounded tissue with organoid plugs in place.

FIG. 3b illustrates the condition of the plug and ovarian pathway after the wound healing process has proceeded to the extent permitted by the continued presence of the plug. The several layers of the target site of the pathway have healed to form healing granulation tissue around the plug and throughout the wounded pathway. Placement of the plug directly against the wounded inner surface of the pathway has encouraged this tissue to surround the plug, and prevented epithelium from forming around the longitudinal surfaces of the plug. Epithelium 26 has grown to cover the distal and proximal faces of the plug to form distal and proximal layers of tissue over the plug. The unwounded longitudinal muscle layer and remaining circular muscle layer remain in the pre-wound condition. After a period of time, a network of new blood vessels organizes within the granulation tissue, and a matrix of connective tissue forms within the granulation tissue. FIG. 3c illustrates the condition of the large pore plug and ovarian pathway after the wound healing process has proceeded to the extent permitted by the continued presence of the plug. The several layers of the target site of the pathway have healed to form healing granulation tissue around the plug and throughout the wounded pathway. Placement of the plug directly against the wounded inner surface of the pathway after wounding has encouraged this tissue to surround the plug, and encouraged healing tissue penetration into the plug (and thus inhibited epithelium from forming around the longitudinal surfaces of the plug). Numerous blood vessels 36 have entered or formed within the large pores. The prior entry of wound healing tissue, including numerous macrophages 37, has inhibited formulation of a fibrous capsule around the plug and epithelial intrusion between the plug and the wounded portion of the ovarian pathway. The body appears to recognize the plug as an organ, and foregoes additional wound healing and foreign body reactions.

Figure 3D:
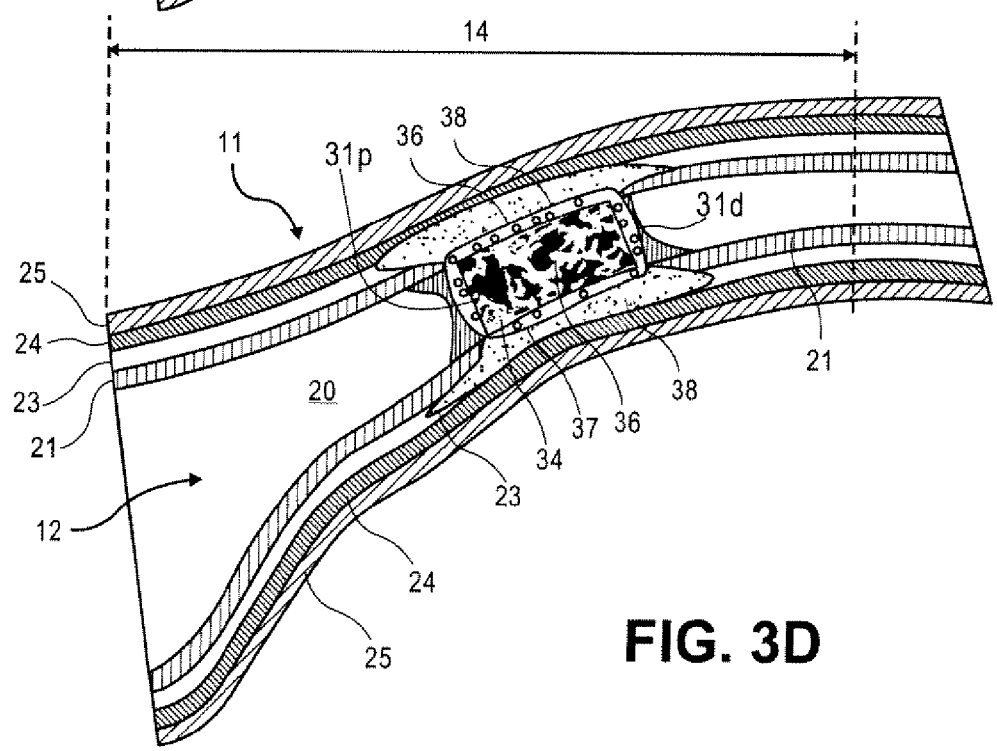

FIG. 3d illustrates the condition of the small pore plug and ovarian pathway after the wound healing process has proceeded to the extent permitted by the continued presence of the plug. The several layers of the target site of the pathway have healed to form healing granulation tissue around the plug and throughout the wounded pathway. Placement of the plug directly against the wounded inner surface of the pathway after wounding has encouraged this tissue to surround the plug, and prevented epithelium from forming around the longitudinal surfaces of the plug. Scattered macrophages 37 have entered the small pores, and a vascularized altered foreign body capsule 38 has formed around the plug. The vascularized foreign body capsule includes numerous blood vessels, and further progress of the foreign body response is inhibited. Epithelium has grown to cover the distal and proximal faces of the plug to form distal and proximal layers of tissue over the plug.

Thus, depending on the pore size of the plug foam, the plug may be infiltrated with vascularized granulation tissue (for plugs with large pore sizes in the range of 40-200 microns) or infiltrated with scattered macrophages and surrounded with a vascularized capsule of connective tissue (for plugs with small pore sizes in the range of 1-20 microns). In either case, the growth of epithelium between the plug and the wounded portion of the ovarian pathway is inhibited, and the formation of a foreign body avascular fibrous capsule is inhibited by displacement of that structure in favor of other wound healing structures.

The plug is preferably made of a material with a pore size, chemistry and architecture that actually facilitates cellular ingrowth into the material (large pore plugs) or that allow macrophage infiltration but inhibit cellular ingrowth (small pore plugs). Regarding the large pore plugs, the nature of the desired ingrowth is vastly different from the standard foreign body reaction. The primary difference is a type of ingrowth that consists of a variety of blood vessels, connective matrix and cells, macrophages, and other cells. Regarding the small pore plugs, the nature of the foreign body capsule is altered to include numerous blood vessels. These structures can be described as "organoid," as they exist as an integral part of the organ. Two types of materials have displayed this organoid appearance after healing, those materials with a specified architecture and pore size of between 40-200 microns, and those materials that have specific architectures and are microporous (1-20 microns). The wound healing growth would be classified histologically for the small pore materials as resembling the tissue of an "altered foreign body response", and for the larger pore materials, as approaching the look and content of the "dermis".

The plug may be made of ePTFE (also referred to as expanded Teflon™ or expanded polytetraflouroethylene), porous silicone, acrylic copolymer, cellulose acetate, polyethylene and high density polyethylene (HDPE), PE, polyester, and sintered, micro-knurled, or molded titanium and platinum. Textured polyamides or polyimides, hydroxyapitite, and hydrogels are also potential suitable materials. Preferably, these materials are formed into a plug (a sphere, cylinder or other occluding mass) of foamed material. The preferable pore sizes of the foam fall into the two distinct ranges mentioned above, namely 1-20 micron pore size and 40-200 micron pore size (40-120 microns is even better). The foam is preferably formed as a reticulated foam, meaning that the pores communicate with other pores, rather than existing as discrete and isolated voids within the material. The plug may have a solid core surrounded by foam or a porous material having a reticulated network of pores.

Silicone foam is readily formed into foam plugs with the procedure set forth in Seare, Method of Making A Porous Device, U.S. Pat. No. 5,605,693 (Feb. 25, 1997). Uncured silicone (MED 4860 grade supplied by Nusil Technology Corp is suitable) is injected into a form packed with granules, and slowly fills the voids between all the granules. The silicone is cured and the particles are dissolved in a suitable solvent (water, where sugar or salt is used) to form the reticulated foam plug. The foam plug has a durometer value between 20-100 Shore A, preferably about 60 Shore A. The foam is a matrix of interlocking angular blocks of silicone which are formed together to create a network of communicating pores with sizes corresponding to the size of the granules that were used to make the negative. The pores communicate with surrounding pores to form a reticulated or networked foam. The pore size of the large foam pores are in the range of 40-200 microns (mu). The structure of small pore foam is essentially the same as large pore foam, except that the pore sizes is in the range of 1-20 microns.

The plug may be fabricated from expanded polytetraflouroethylene, commonly referred to as ePTFE, with the processes used for forming ePTFE generally. Starting with a PTFE rod, the rod is stretched to expand the PTFE to form the system of nodes and fibrils characteristic of ePTFE. Pore size (commonly referring to the distance between the nodes) and the number and size of fibrils connecting the nodes is controlled by stretching the PTFE rods at controlled rates and temperatures. (The plugs may also be fabricated from sheets of PTFE which are stretched to the degree necessary to create the desired porosity, then cut to shape. The plugs may also be formed of very thin sheets of ePTFE which are used to coat or wrap a solid rod of PTFE.) The process results in a material having microstructure characterized by elongate nodes interconnected by fibrils running between the nodes and extending generally perpendicular to the long dimension of the nodes. The pore size, as measured between the nodes, is in the range of 40 to 200 microns for large pore foam and 1 to 10 microns for small pore foam.

The plug may also be formed of acrylic copolymer (such as tetrafluoroethylene and hexafluoropropylene). The acrylic copolymer is formed as a mass of interlocking fibers, which on the outer surface of the foam become outwardly extending rods. The pore size, as measured by the distance between the rods is preferably in the range of 1 to 10 microns.

The plug may be formed of a shape memory polymer, one example being compound polymer of oligo(ε-caprolactone)diol and crystallisable oligo(ρ-dioxanone)diol. In use, the plug may be formed in a foam structure, compressed into a smaller form and delivered into the fallopian tube. Upon heating the plug would form into the expanded plug. This is particularly advantageous because it would allow a lower profile delivery system, and shape memory polymers requires lower temperatures (slightly above body temperature) than shape memory alloys to regain form.

The plug may be fabricated with the polymer materials described herein and additionally doped with radiopaque elements such as barium sulfate. Radiopaque fillers such as tungsten, tungsten dioxide, tungsten trioxide, stainless steel powder, silver iodide, or iodinated organic compounds may also be used. Fillers in powder, sphere, particle, or flake form may be used. A radiopaque stripe may also be applied to one side of the plug, or upon the entire outer surface. In certain embodiments, the plug may include a combination of markers, such as at least one visual marker (observable with an endoscope) at least one radiopaque marker (observable with x-ray imaging) and at least one echogenic marker (observable with ultrasound imaging methods). In other embodiments, a plug may include a combination of two of these types of markers such as a combination of a visual marker and a radiopaque marker, or a combination of a visual marker and a echogenic marker, or a combination of a radiopaque marker and an echogenic marker. In other embodiments, a plug may include only one type of marker (e.g. either a visual marker or an echogenic marker or a radiopaque marker).

The entirety of the implant may be additionally doped or coated with substances which are antimicrobial in nature. Silver-based micro particles, (e.g. silver bromide) may be embedded in the plug matrix. Additionally, chemicals such as chitosan may be used to prevent bacterial infections and prevent the growth of a biofilm.

Figure 4A:
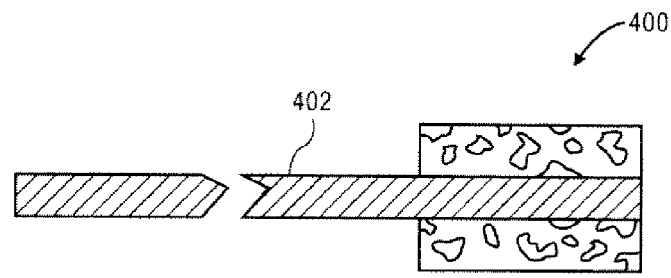
FIG. 4a is a cross section of a plug including a tail.

FIG. 4a shows an example of a plug 400 including a tail 402. The plug may be constructed as described above (e.g. with porous foam). A shown the tail 402 extends throughout the plug 400, however the tail 402 may also terminate at a portion approximately midway through the plug. The tail 402 serves as a marker, which may be a visual marker. After delivery into the ovarian pathway, the tail 402 is visible past the ostium, thus a physician may visibly confirm the successful delivery of the plug. Thus, the presence of the tail 402 greatly reduces the chance of unilateral plug delivery. The tail 402 may be constructed from a polymer material, for example a standard suture material. The tail 402 may also be formed from a biodegradable polymer for example a glycolic or lactic acid derived polymer may be used. The tail 402 may also be formed from a metallic alloy such as stainless steel, gold, or platinum so as to be visible under an x-ray examination. A nickel-titanium alloy (nitinol) may also be used. A coating of titanium-nitride may also be used over a metallic alloy in order aid in visibility. Titanium-nitride may be coated in different colors, for example blue with a coating thickness of 60 nm, to aid in visible contrast. The tail 402 or plug 400 may also include an echogenic marker, such as gas bubbles trapped in a substance. The tail 402 may also be cut off after proper insertion.

Figure 4B:
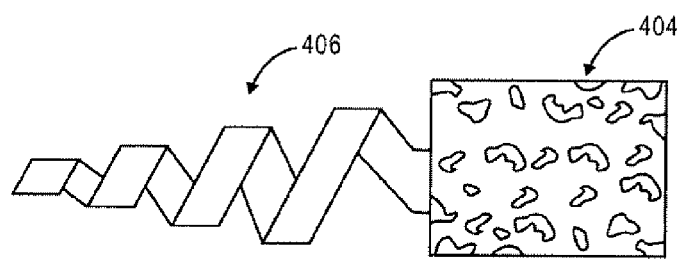
FIG. 4b is a side view of a plug including a coiled tail.

FIG. 4b shows an example of a plug 404 including a coiled tail 406. The plug 404 may be constructed as described above (e.g. with porous foam). A coiled tail may be packaged in a wound configuration and thus a more compact configuration prior to delivery. The coiled tail 406 also has a large surface area and thus is easy visible under direct and x-ray observation. The coiled tail 406 may be constructed from the same materials as the tail 402 above. The coiled tail 406 may be constructed from flat or round wire. Thin, flat wires are advantageous due to a low profile, and ease of deflection, thus may be less likely to irritate the ovarian pathway. The coil may be self expanding and serve as an anchor which resiliently presses against an inner wall of the ovarian pathway. The coiled tail 406 may also be cut off after proper insertion.

Figure 4C:
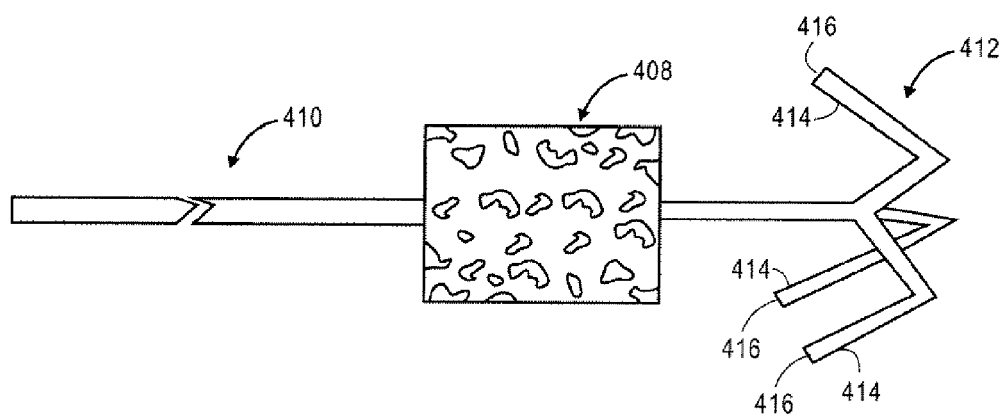
FIG. 4c is a side view of a plug including a tail and an embodiment of an anchor.

FIG. 4c shows an example of a plug 408 including a tail 410 and an anchor mechanism 412. The plug 408 may be constructed as described above (e.g. with porous foam). The anchor mechanism 412 includes three anchors 414 as shown, but may include more or less anchors 414. The anchor mechanism 412 needs at least one anchor 414 to function. The anchors 414 serve to prevent movement of the plug when placed in the fallopian tube. The tips 416 of the achors 414 place a radial stress onto the fallopian tube wall and thereby lock the plug 408 into place. The anchor mechanism 412 may have two states, a folded state (not shown) and an expanded state as shown. The anchor mechanism 412 may be constructed from an alloy such as stainless steel, nitinol with super elastic properties, or a shape-memory alloy. The anchor mechanism may be a super elastic alloy and expanded by physical release from the folded state. Alternatively the anchor mechanism may be a shape memory alloy or shape memory polymer and heated to the expanded state. Alternatively the anchor mechanism may be a malleable material and physically deformed into the expanded state, for example by balloon expansion. Alternatively the anchor mechanism 412 is constructed from a biodegradable polymer material.

Figure 5A:
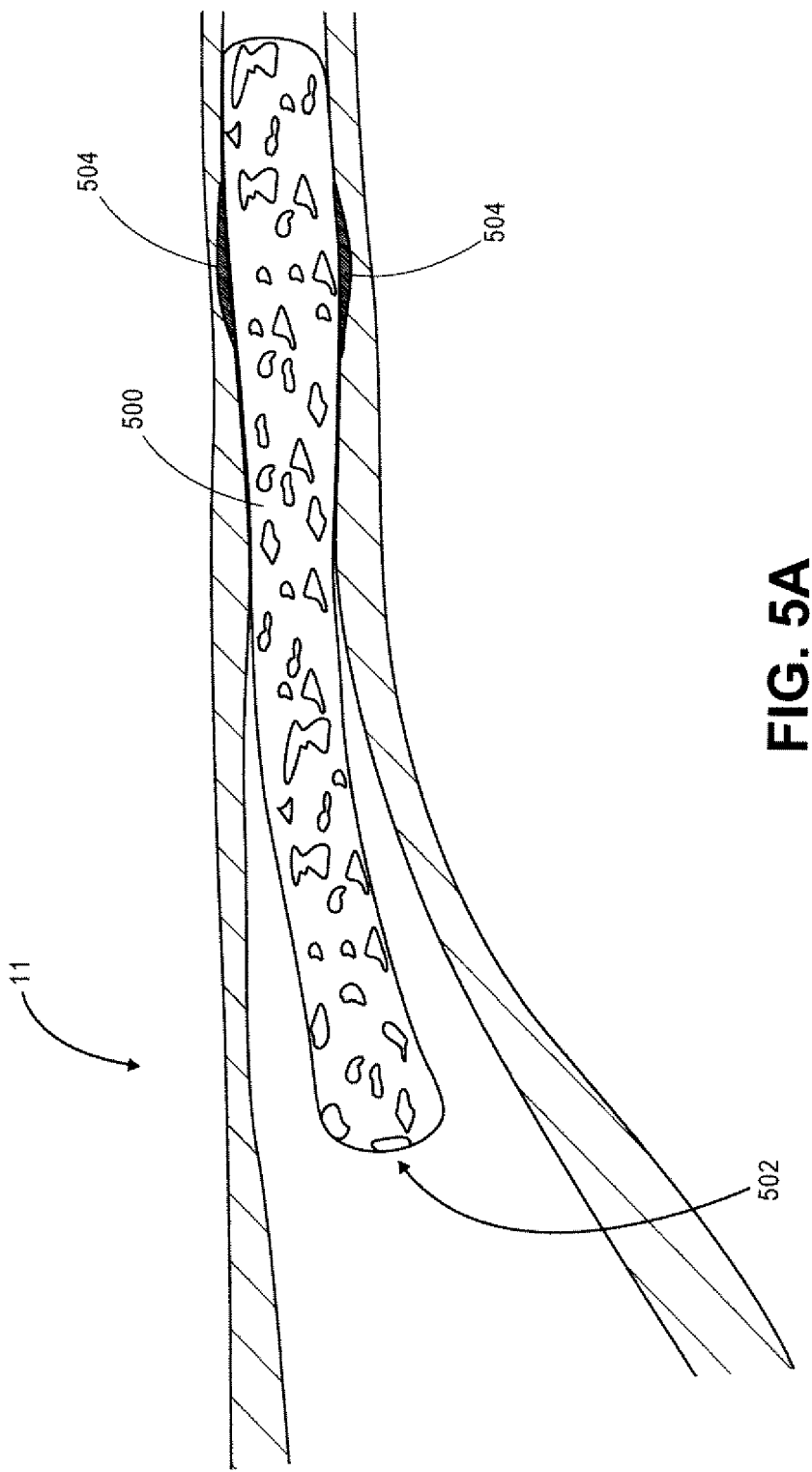
FIG. 5a is a cross section of an ovarian pathway including an elongated plug.

FIG. 5a shows an example of an elongated plug 500 positioned in the utero-tubal junction 11. The plug may be constructed as described above (e.g. with porous foam). The elongated plug 500 may be positioned as shown or alternatively deeper within the ovarian pathway. The elongated plug is advantageous because the proximal end 502 serves as a marker, thus the elongated plug 500 does not require an additional tail element, although alternatively a tail element may be added. A tail element may be helpful for visualization if the elongated plug 500 is positioned deep within the ovarian pathway. The elongated plug 500 may be 2.5 cm in length, or in a range from 4 mm to 4 cm in length. The elongated plug 500 is less prone to operator placement error because it requires less precession in placement as the length of the elongated plug 500 is greater than the length of damaged area 504 in the fallopian tube as shown. The damaged area 504 may be wounded through application of energy to the area as described herein, and may be deeper, for example approximately 1 cm past the ostium. Thus there is a very high likelihood that portion of the elongated plug 500 will always be in contact with the damaged portion of the fallopian tube for proper tissue in growth in to the elongated plug 500. This embodiment is one example in which the size of the damaged area is substantially different (e.g. greater than 100% different) than the size of the plug which is placed in the damaged area. In another embodiment, the damaged area is substantially larger (e.g. at least twice the size) than the size of the plug.

Figure 5B:
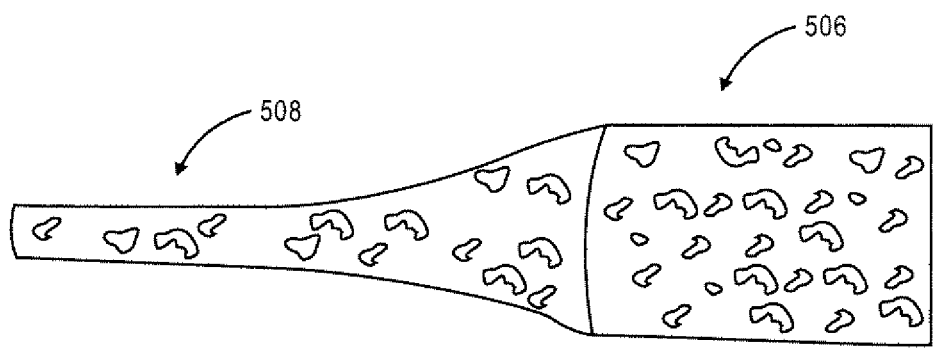
FIGS. 5b and 5c are side views of elongated plugs.

FIG. 5b shows an example of an alternate elongated plug 506. The plug may be constructed as described above (e.g. with porous foam). The elongated plug 506 may be positioned as shown in FIG. 5a or alternatively deeper within the ovarian pathway. The elongated plug is advantageous because the tapered proximal end 508 serves as a marker; thus the elongated plug 506 does not require an additional tail element, although alternatively a tail element may be added. A tail element may be helpful for visualization if the elongated plug 500 is positioned deep within the ovarian pathway.

The tapered proximal end 508 is tapered to a reduced diameter. The tapered proximal end 508 is offers less contact with the utero-tubal junction and thus may cause less of a foreign body response or less irritation to the utero-tubal junction.

Figure 5C:
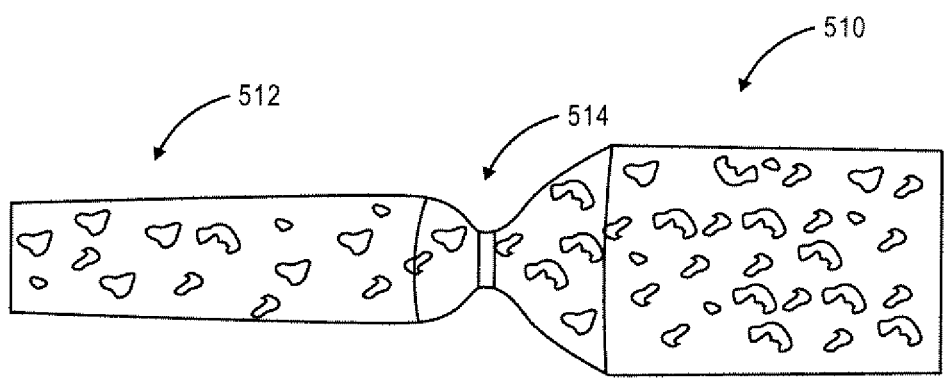

FIG. 5c shows an example of an alternate elongated plug 510. The elongated plug 510 may be positioned as shown in FIG. 5a or alternatively deeper within the ovarian pathway. The elongated plug is advantageous because the reduced proximal end 512 serves as a marker, thus the elongated plug 510 does not require an additional tail element, although alternatively a tail element may be added. A tail element may be helpful for visualization if the elongated plug 500 is positioned deep within the ovarian pathway. The reduced proximal end 512 is tapered to a reduced diameter. The reduced proximal end 510 is offers less contact with the utero-tubal junction and thus may cause less of a foreign body response. The elongated plug 510 features a tear-away joint 514. The tear-away joint allows a later removal (e.g. 3 months after insertion) of the reduced proximal end 512 after the elongated plug 510 has been secured to the fallopian tube, because the proximal end may have no further use after tissue has grown into the elongated plug. The tear-away joint features the smallest cross section of material of the elongated plug 510, thus a pulling force in the proximal direction will result in proximal end 512 severing from the rest of the elongated plug 510 at the tear-away joint 514. The proximal end 512 may be removed by endoscope forceps in conjunction with an endoscope or forceps under fluoroscopy.

FIG. 5d shows an example of an alternate elongated plug 516. The elongated plug includes an elongated mid-section 518 which is has a smaller cross-sectional area than end portions 520. The mid-section 518 may range in length from 1-20 mm and have an outer diameter of 0.5-1.5 mm. The length of the plug 516 may range from 1 mm to 4 cm, with a preferred length between 3-4 mm. The diameter of the end portions 520 may be as large as 2.6 mm. The end portions 520 are compressible before delivery into a fallopian tube and serve as anchoring mechanisms by placing diametrical expansive force onto the fallopian tube walls, which is larger than force exhibited by the mid-section 518. Two end portions are shown, but this is merely demonstrative as only one, or at least one end portion is required. The plug 516 also includes a tail element 522 as described elsewhere herein, which may be flexible, semi-rigid, or rigid.

FIG. 5e shows an example of an alternate elongated plug 524. The plug features an elongated mid-section 526 and expandable hollow end portions 528. The plug shares the general dimensions with plug 516 of FIG. 5d. The hollow end portions 528 are conically shaped and also hollow for easier compressibility before delivery, and have a larger cross-sectional profile than the mid-section 526, but not necessarily a larger cross-sectional area. Additionally the hollow portions may serve to deliver drugs such as hormones, spermicidal, marker dyes, or scar tissue inducing agents. The end portions 528 may also include hoops 529 or a mesh structure (not shown) coupled to or within the end portions 528, which would serve to spring the end portions 528 open from a compressed state and provide anchoring force for the plug 524. The hoops or mesh structure may be constructed from superelastic, or shape memory alloy or shape memory polymer, or from an expandable and malleable alloy or polymer, and also be a radiopaque material or doped with radiopaque elements. The plug 524 may also include a tail element as described herein.

FIG. 5eI and 5eII show end views of plug 524. FIG. 5eI shows the plug 524 in a normal state, the hollow portion is clearly visible. FIG. 5eII shows the plug 524 in a compressed state. The plug 524 may be compressed by applying circumferential force tangential to the longest axis, such as placing the device in a small delivery lumen. The plug 524 may also be a shape memory material and compressed into the state shown in FIG. 5eII before heating and expanding the plug 524 in the state shown in FIG. 5eI. The plug may also be a hydrogel material, and thus FIG. 5eII would be a dry state, upon which the addition of fluids (e.g. saline, water) the plug 524 would expand to the state shown in FIG. 5eI.

Figure 5F:
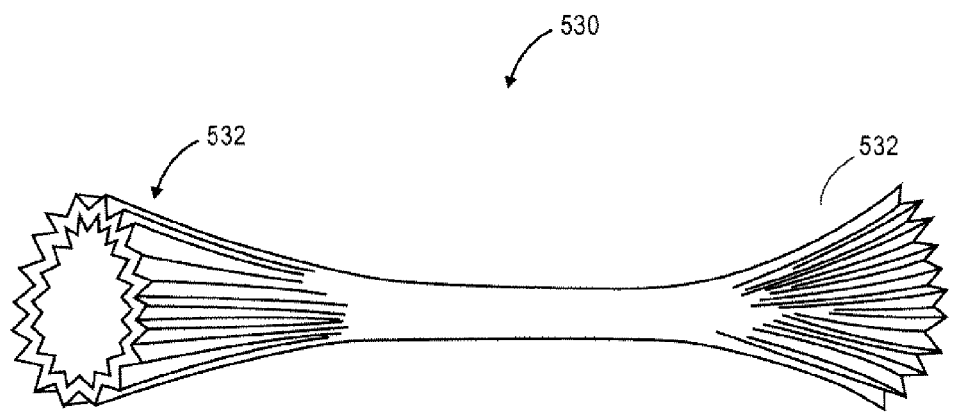
FIG. 5f is a side view of an elongated plug.

FIG. 5f shows an example of an alternate elongated plug 530. The plug shares the same general construction of plug 524 as shown in FIG. 5e, with the exception of the hollow end portions 532 which include an accordion wall. The end portions are capable of folding down to a narrow profile in order to be placed into a small lumen prior to delivery into a fallopian tube, which is particularly advantageous because it allows the use of a smaller delivery catheter.

Figure 5G:
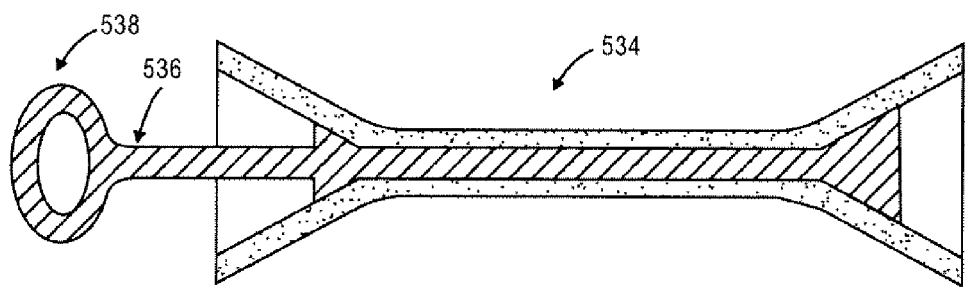
FIG. 5g is a cross section of an elongated plug.

FIG. 5g shows an example of an alternate elongated plug 534. The plug 534 shares the same general external profile of plug 524 shown in FIG. 5e, with the exception that plug 534 is molded around insert 536. Insert 536 allows subsequent removal or replacement of plug 534 after placement within a fallopian tube. The insert includes a pullable and pushable loop 538 for replacement or removal of the plug 534. The insert may be constructed from a variety of materials, including metals and polymers, but should generally be a stiffer material than the plug material. In use the plug 534 would be placed in a fallopian tube as generally described herein, and then graspers may be used to clamp onto the loop 536 for replacement or removal, which is particularly advantageous because incorrect placement of the plug 534 may result in an ineffective closure of a fallopian tube.

Figure 5H:
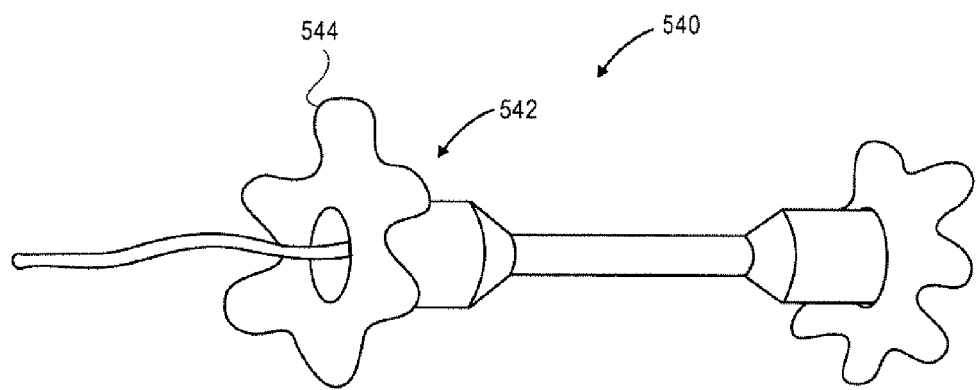
FIG. 5h is a side view of an elongated plug.

FIG. 5h shows an example of an alternate elongated plug 540. The plug 540 shares the same general construction of plug 524 shown in FIG. 5e, however the conical ends portions 542 feature flower shaped ends 544. The flower shaped ends 544 provide an irregular contour which provides anchoring force against the fallopian tube walls. This is particularly advantageous because the cross-sectional profile of the fallopian tube is also irregular, thus the flower ends 544 may provide a better anchoring mechanism than a round profile.

Figure 5I:
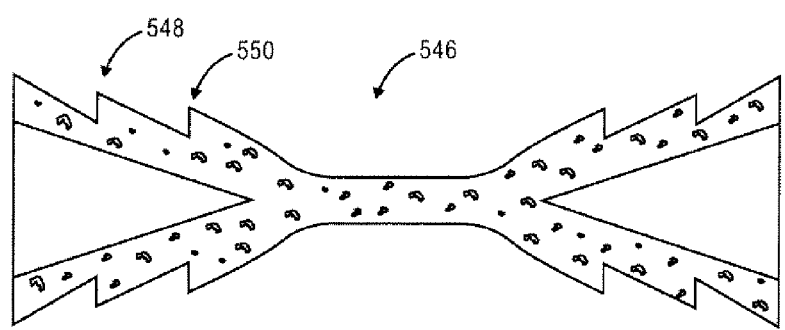
FIGS. 5i and 5j are cross sectional views of elongated plugs.

FIG. 5i shows an example of an alternate elongated plug 546. The plug 540 shares the same general construction of plug 524 shown in FIG. 5e, however the end portions 548 feature layers 550 which provide additional anchoring against a fallopian tube wall. In use the layers 550 provide advantageous opposing forces on both sides of the plug 546 to help prevent migration of the plug before tissue ingrowth occurs. Three layers are shown on each side of the plug 546, however this is merely demonstrative and more or less layers may be used.

Figure 5J:
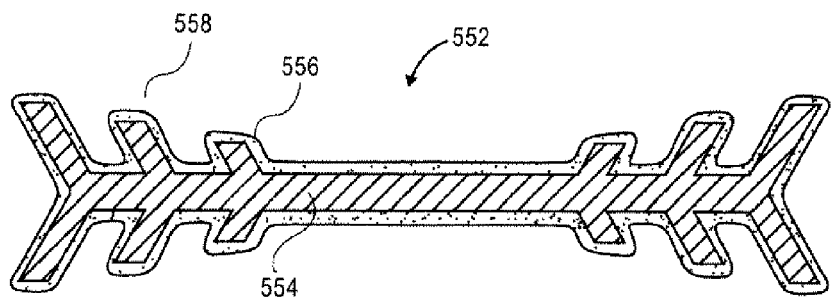

FIG. 5j shows an example of an alternate elongated plug 552. The plug 552 features a frame 554 with foam mold 556. The foam mold 556 may be porous as described elsewhere herein. The frame 554 may be constructed from a superelastic or shape memory alloy/polymer. The frame 554 may also be constructed from a standard alloy or polymer. The plug includes barbs 558 which provide opposing anchoring force on the plug when placed within a fallopian tube.

The delivery catheter developed for delivery of the plugs and to apply the desired wounding system is illustrated in FIG. 6a. FIG. 6a illustrates an embodiment in which the wounding energy source is RF energy. The catheter includes a catheter body 51 with a wounding segment 52 comprising a short tubular extension slidably mounted within the distal tip 53 of the catheter. The distal tip of the catheter body extends over the proximal end of the tubular extension for a short length of 2-25 mm, which is sufficient to firmly hold the tubular extension during use. Four electrodes 54, 55, 56 and 57 are aligned along the outer surface of the wounding segment. One or more temperature sensors 58 are mounted on the wounding segment (a single temperature sensor may be mounted in the center of wounding segment, between the ground electrodes). The distal tip and wounding segment are about 55 mil in outer diameter. The wounding segment in the RF embodiment may be about 6 to 8 mm long, and the electrodes are ring electrodes which are about 0.037 to 0.050 inches wide (measured along of the longitudinal axis of the catheter) and wrap around the catheter. Alternatively the wounding segment may include more electrodes over a range from 8 mm-4 cm in length to accommodate longer plugs. One or more foam plugs 34 are stored within the catheter body, and are shown housed within the wounding segment. By arranging the electrodes with the energized or hot electrodes 54 and 57 on the distal and proximal ends of the wounding segment, with the ground electrodes 55 and 56 situated between the hot electrodes, a long and shallow lesion may be produced in the ovarian pathway when the electrodes are energized appropriately. The converse pattern of ground electrodes located on the distal and proximal ends of the wounding segment with energized electrodes located between the ground electrodes may also be used to create the desired long and shallow lesion.

The plugs may be compressed to fit into the lumen 59 in the wounding segment of the catheter. A holding rod 60 is disposed within the catheter body 51, fixed longitudinally within the catheter body at any point distal to the wounding segment (it may be secured by gluing or heat sealing a proximal segment of the holding rod to the inner wall of the catheter body) which permits adequate pullback of the wounding segment to release the plug. A pullwire 61 is secured to the proximal end of the wounding segment by attachment of the boss 62 on the distal end of the pullwire. The pullwire extends distally from the wounding segment to the proximal end of the catheter body. FIG. 6b shows the cross section of the device along section 6b, more clearly illustrating the relative positions of the pullwire boss 62 fixed to the inner wall of the wounding segment 52, which itself is slidably disposed within the distal tip 53 of the catheter body 51, and also slidably disposed around the holding rod 60. FIG. 6c shows the cross section of the device along cross section 5b, more clearly illustrating the position of the holding rod 60 within the catheter body 51. The pullwire 61 can be manipulated by hand from the proximal end of the catheter to pull the wounding segment proximally within the catheter body. The holding rod 60 maintains the plug (or plugs) in position within the ovarian pathway while the wounding segment is pulled proximally, thereby ejecting the plugs from the distal tip of the catheter without moving them relative to the wounded segment of the ovarian pathway after initial positioning (and also without moving the catheter body relative to the patient). Electrical wires which supply RF power to the electrodes may run the through the lumen of the catheter body alongside the pullwire or they may be housed within the catheter body, and an electrical connector 63 is supplied on the proximal end of the catheter to connect the wires in the catheter to the RF power supply. The electrical wires may also be incorporated into the pullwire, with the electrical connections to the RF power supply being disposed on the proximal end of the pullwire. Other wounding mechanisms may be employed, including resistive heating elements, direct laser irradiation, laser heated elements, microwave, ultrasound, peizo-electric abrasion, hypothermia, cryothermia, chemical ablation, and mechanical and physical abrasion.

Figure 6D:
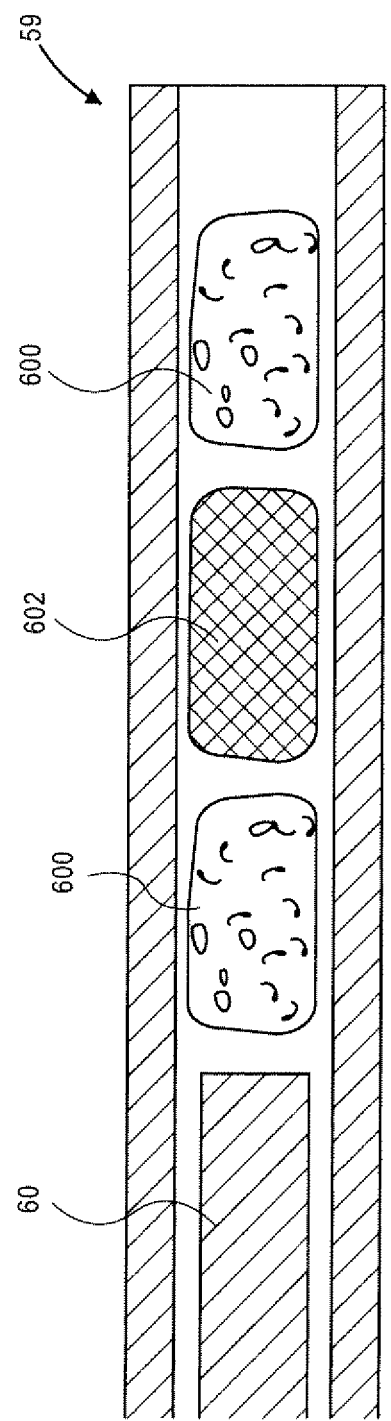

FIG. 6d shows a cross sectional alternate arrangement of the catheter as described above. The lumen 59 and the holding rod 60 operate largely as described above. The catheter includes two plug implants 600. The implants may include tails and/or anchors as described previously herein. A pellet 602 is spaced between the plugs 600 to operate as a marker element or visual cue, to the operator, that a plug has been successfully placed. No visual indicators of positive plug placement previously existed, thus it has been found that two plugs have been mistakenly placed in one fallopian tube, possibly resulting in later pregnancy and required retreatment. The pellet 602 may help prevent the placement of two plugs into one fallopian tube. In use the operator would place one plug 600 into one fallopian tube, then remove the catheter from the fallopian tube, and observe the ejection of the pellet. Thus the ejection of the pellet would confirm to the operator that only one plug 600 has been properly placed within one fallopian tube. The operator may then safely continue to the next fallopian tube for placement of the next plug 600. The pellet 602 may be constructed from a biologically inert substance such as non-porous silicone or non-porous PTFE which would eventually be naturally flushed from the body or removed with forceps. Alternatively the pellet 602 may be constructed from a harmless rapidly biodegradable substance, such as gelatin or cornstarch based foam. The pellet 602 may be colored to provide more contrast with the surrounding uterus structure, for example green. The pellet 602 may also be a dye-filled capsule, which would provide visual confirmation by observing dye exiting the patient.

Figure 6E:
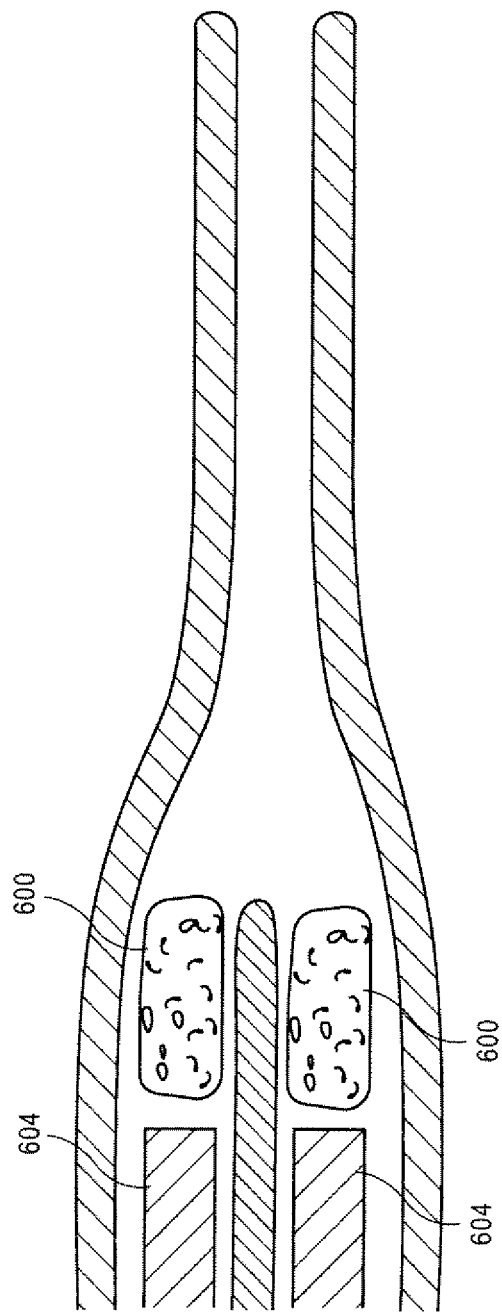
Figure 6F:
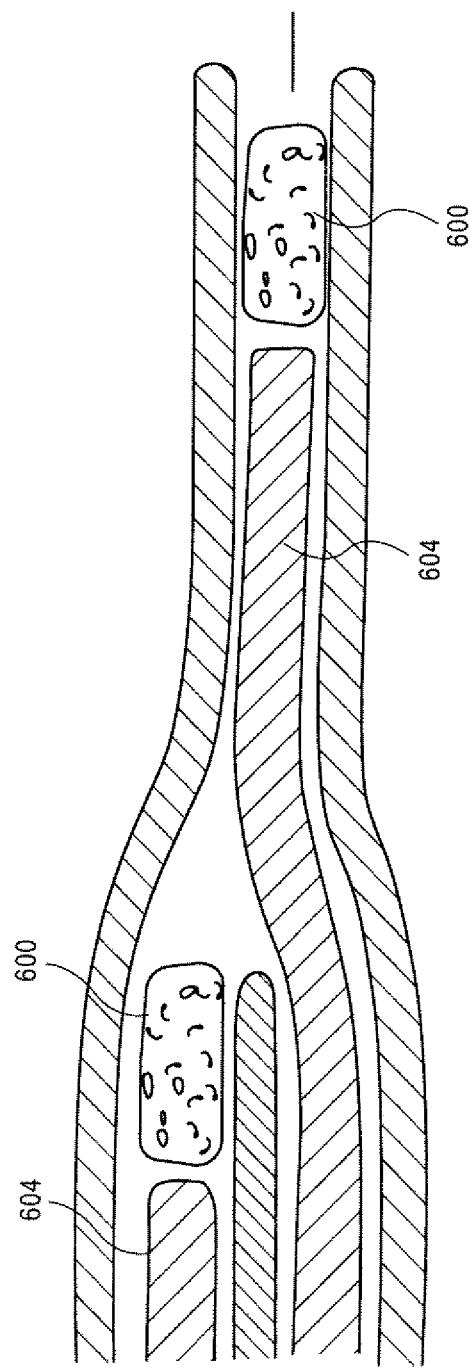

FIGS. 6e and 6f show cross sectional alternate arrangements of the catheter as described above. The catheter shows a unique side by side arrangement of the implants 600, with a dual lumen segment necking down to a single lumen segment. The implants may include tails and/or anchors as described previously herein. Each implant has a holding rod 604 for pushing the implant out of the catheter. In use one implant is pushed out of the catheter while the other remains in side a separate lumen, as shown in FIG. 6f. This is particularly advantageous because it allows the low profile delivery tip of device, as shown in FIG. 6, and it greatly reduces the risk of pushing two implants into one fallopian tube because the holding rods would be operated by separate mechanisms on a handle, which is not shown.

In use, the catheter is inserted into the uterus transcervally, and the distal tip of the catheter is navigated into the fallopian tubes, until the wounding segment is stationed at the desired point along the ovarian pathway. Surgeons may view the placement with an endoscope or hysteroscope, and/or placement within the pathway can be confirmed with fluoroscopy or ultrasound energy. (Of course, placement of the catheter may be accomplished blindly, using tactile feedback only.) Once the wounding element is in place, the appropriate wound may be created by application of power limited so as destroy the epithelial layer/endosalpinx in the area of plug placement, yet avoid unwanted physiological reactions. The goal is to completely necrose the epithelium/endosalpinx, and to accomplish this goal, the surgeon applies sufficient wounding power to necrose the epithelium/endosalpinx, and the lamina propria, while limiting the wounding power to prevent damage to the longitudinal muscle layer. Damage to the circular muscle layer should be insubstantial, but may be tolerated. After wounding the ovarian pathway, the wounding segment is withdrawn by pulling the pullwire proximally while holding the catheter in place. This ejects the plug without need for relative motion between the plug and the wound after the operator has positioned the catheter for use.

When using RF energy as the wounding mechanism, it has been determined that power of 0.1 to 5 watts for about 5 to 60 seconds causes thermal necrosis of the epithelial layer, without damaging the longitudinal muscle layer and without inducing an acute inflammatory response. Preferably, temperature in the tissue is monitored with temperature sensors mounted on the delivery catheter wounding segment, and power is applied to maintain tissue temperature in the range of 40-80° C. for a period of 5 to 60 seconds, or as long as 80 seconds. It has determined that 64° C. for a period of 60 seconds works well in human patients.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. An occluding device for occluding a body lumen comprising:
   a porous polymer plug;
   a proximal expandable hoop within a proximal end portion of the plug; and
   a distal expandable hoop within a distal end portion of the plug;
   wherein the proximal and distal expandable hoops serve to spring the proximal and distal end portions open from a compressed state to an expanded state and provide a proximal and distal anchoring forces for the plug.

2. The occluding device of claim 1, wherein a mid-section of the plug has a smaller cross-sectional profile than the proximal and distal end portions of the plug when in the expanded state.

3. The occluding device of claim 2, wherein the proximal and distal hoops are constructed from a superelastic or shape memory material.

4. The occluding device of claim 3, wherein the proximal and distal hoops are constructed from a metal alloy.

5. The occluding device of claim 3, wherein the proximal and distal hoops are constructed from a polymer.

6. The occluding device of claim 2, wherein the proximal and distal end portions are conically shaped.

7. The occluding device of claim 2, wherein one of the proximal and distal expandable hoops is doped with radiopaque particles.

8. The occluding device of claim 1, further comprising a tail element coupled with the porous polymer plug.

9. The occluding device of claim 8, wherein the tail element is flexible.

10. The occluding device of claim 1, wherein the porous polymer plug comprises silicone.

11. The occluding device of claim 1, wherein the silicone is doped with radiopaque particles.

12. The occluding device of claim 1, wherein the plug comprises gas bubbles trapped in a substance.

* * * * *